United States Patent [19]
Greenwald

[11] Patent Number: 5,486,519
[45] Date of Patent: Jan. 23, 1996

[54] METHOD FOR TREATMENT OF ACUTE RENAL FAILURE

[76] Inventor: James E. Greenwald, 100 N. Euclid Ave., Ste. 902, St. Louis, Mo. 63108

[21] Appl. No.: 293,989

[22] Filed: Aug. 22, 1994

[51] Int. Cl.$^6$ ............................................. A61K 31/505
[52] U.S. Cl. ........................................................ 514/258
[58] Field of Search ............................................ 514/258

[56] References Cited

U.S. PATENT DOCUMENTS 4,496,544   1/1985   Needleman ................................ 514/13

OTHER PUBLICATIONS

Dundore, et al., Eur. J. Pharmacol. 249, 293–297 (1993).
McMahon, et al., J. Pharmacol. Exp. Therap. 251, 1000–1005 (1989).
Buchholz, et al., Fed. Am. Soc. Exp. Biol. J3, A1186 (1989).
Lugnier, et al., Am. J. Physiol. 262, H654–H660 (1992).
Burns, Chem. Absts. 117: 22314 (1992).
Needleman, et al., Hypertension 7, 469–482 (1985).
Cole, et al., J. Clin. Invest. 76(G), 2413–2415 (1985).
Needleman & Greenwald, New England J. Med. 314, 820–834 (1986).
Needleman, Fed. Proc. 45(7) 2096–2100 (1986).
Medline Abstract 92370201: Soales–da–Silva et al, "Effect of Alpha–Human Atrial Natriurtr Peptide on Synthesis of Dynamics in The Rat Kidney," *Br J. Pharmacol.* (1992 Apr.) 105(4) 869–74.

*Primary Examiner*—Zohreh Fay
*Assistant Examiner*—Keith MacMillan
*Attorney, Agent, or Firm*—Scott J. Meyer

[57] ABSTRACT

A method is disclosed for treatment of acute renal failure which comprises administering to a warm-blooded mammal manifesting acute renal failure a small but effective amount of zaprinast sufficient to effect acceleration of recovery from said acute renal failure.

4 Claims, 4 Drawing Sheets

METHOD FOR TREATMENT OF ACUTE RENAL FAILURE

BACKGROUND OF THE INVENTION

The present invention relates to a method for the treatment of acute renal failure (ARF) and, more particularly, to a method for improving the recovery from acute renal failure by treatment with zaprinast. (Note: Literature references on the following background information and on the conventional test methods and laboratory procedures well known to the ordinary person skilled in the art and other such state-of-the-art techniques as used herein are indicated in parentheses and appended at the end of the specification.)

Acute renal failure (ARF) is a major problem in contemporary medicine.

Five percent (5%) of all hospitalized patients are affected by some degree of acute renal dysfunction (1).

Fifty percent (50%) of all patients diagnosed with ARF will die, thus demonstrating the morbidity and mortality associated with this disease (2).

In various clinical situations, such as intensive care medicine, post cardiovascular surgery, and after cadaveric renal transplantation, the incidence of acute renal failure has been reported to be between 50% and 75% (1,3).

Under most conditions, it is not possible to predict who will develop ARF. Thus, identification of a pharmacologic intervention that would be effective in the treatment of established renal failure would be a significant therapeutic breakthrough. The kidney is a remarkably regenerative organ. A significant decrease in renal artery blood flow will result in severe tubular epithelial cell destruction, intrarenal hemorrhage, and a prolonged decrease in glomerular filtration rate (GFR).

The decrease in GFR is most likely a result of both tubular obstruction and afferent arteriolar vasoconstriction (4).

In most circumstances, the kidney will recover from such an insult; however, in many cases, recovery does not occur prior to the need for temporary dialysis or the onset of other complications associated with ARF. Numerous non-pharmacologic and pharmacologic strategies have been attempted to enhance recovery from an acute ischemic injury. These include inducing and osmotic diuresis with mannitol, the use of loop diuretics to maintain high tubular urine flow rates, and the low dose infusion of dopamine to increase GFR (1,33,34).

More recently, exogenous administration of peptides such as Atrial Natriuretic Factor (ANF) (9,10,15,16) and insulin-like growth factor I (23,31) have been infused in pharmacologic doses and have accelerated renal recovery and regeneration.

Proposed pathophysiologic mechanisms for ARF include tubular obstruction and/or a reduction in glomerular filtration rate (GFR) (4).

ANF increases GFR and stimulates tubular fluid and sodium flow (5–8); therefore, it should be ideal in the treatment of ischemic ARF.

Recent experimental studies have shown that both ischemic and nephrotoxic ARF may be effectively attenuated by ANF or ANF synthetic analogs administered before or after the onset of renal injury (9–18).

ANF, as well as its synthetic analogs, stimulate the activation of the particulate guanylate cyclase, increase intracellular cGMP production, and cGMP appears to mediate many of the biological functions of ANF (19–21).

Interestingly, inhibition of nitric oxide (NO), an activator of the soluble guanylate cyclase, by L—N$^G$-nitroarginine worsens ischemic renal dysfunction (22,23).

These results indicate that cGMP may be the common denominator responsible for the improvement seen in ARF in response to ANF or NO.

Another potential strategy to increase the intracellular level of cGMP is by inhibiting its degradation to the corresponding nucleoside 5'-monophosphate. This hydrolysis is catalyzed by cyclic nucleotide phosphodiesterases (PDEs) which exist in multiple distinct forms in many tissues (24-27). These PDE isozymes represent the sole mechanism for degrading cGMP and cyclic adenosine monophosphate (cAMP) and therefore play an important role in determining their intracellular concentration.

BRIEF DESCRIPTION OF THE INVENTION

In accordance with the present invention, a method is provided for treatment of acute renal failure (ARF) by administration of zaprinast to a mammalian host manifesting ARF. The zaprinast is administered in a small but effective amount sufficient to accelerate the recovery from said ARF. Zaprinast is the generic name of 1,4-dihydro-5-[2-propoxyphenyl]-7H-1,2,3-triazoylo[4,5-d] pyrimidine-7-one, which also is known chemically as 2-o-propoxyphenyl-8-azapurin-6-one (M&B 22948).

Zaprinast is a known selective inhibitor of the cyclic-GMP-specific-PDE (PDE-V) (28). It elevates intracellular cGMP, produces a dose-dependent decrease in arterial pressure, and also elicits a significant natriuresis (29, 30).

As illustrated herein, zaprinast has been found to be effective in accelerating recovery from established acute renal failure. In humans, ARF is mostly diagnosed only after significant renal dysfunction has already been established. Therefore, the effect of zaprinast is demonstrated herein in a rat model of established ischemic ARF. The test protocol consisted of infusing zaprinast, ANF, or vehicle 24 hours after the acute ischemic insult for a period of only four hours. This protocol is similar to that of Shaw et al. (11), who demonstrated that the combination of urodilatin, an ANF analog, and dopamine improved renal function in ischemic-established ARF.

In illustrative examples using this protocol in the rat species, acute renal failure was induced by sixty (60) minutes of bilateral renal artery clamping. Twenty-four (24) hours after the ischemic insult, rats received either vehicle (5% dextrose), zaprinast (0.03 or 0.3 mg/kg/min) or ANF24 (0.2 µg/kg/min) intravenously for four hours. Renal function, as measured by daily serum creatinine (days 1–7) and day 2 inulin clearances, was dramatically improved by zaprinast but not ANF treatment. Forty-eight (48) hours post renal ischemia, GFR was 0.14±0.04 (mls/min/100 g B.W) in the vehicle and 0.94±0.29 in the zaprinast treated animals. Urinary cGMP was measured to evaluate whether cGMP excretion correlated with renal recovery. During drug infusion, cGMP excretion (fmol/mg creatinine) was 2570±485 and 3709±1014 in the high dose zaprinast and ANF-treated rats respectively. Twenty-four (24) hours after the ANF infusion, urinary cGMP excretion had returned to basal levels. However, forty-eight (48) hours after zaprinast infusion, cGMP excretion was still elevated and did not return to basal levels until 72 hours post infusion. Zaprinast was thus unexpectedly found to be much more effective in the treatment of established ischemic ARF as compared to ANF at the dose studied. Although the increased efficacy of zaprinast versus ANF may be related to its prolonged half-life in established ischemic ARF rats, the inventor is not limited to any particular scientific theory. The actual benefit of zaprinast compared to ANF is its greater potency to stimulate recovery from established ischemic ARF at doses that are less hypotensive.

Although the invention is particularly exemplified hereinbelow with respect to ischemic acute renal failure, it should be understood that it is not limited to ARF caused by ischemic injury but is also applicable to treatment of ARF that may be caused by other factors such as:
1. Hypoperfusion, resulting from sepsis, congestive heart failure, etc;
2. Surgery, e.g., from cross-clamping;
3. Medication, e.g., by inhibitors of angiotensin-converting enzyme (ACE), antibiotics, and drugs causing interstitial nephritis; and
4. Contrast agents used in angiograms and various other diagnostic scans.

It will also be appreciated that although the method of the invention is illustrated in particular hereinbelow with the rat species, it is also useful for other warm-blooded mammals, e.g., humans, in an analogous manner.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in connection with the accompanying drawings.

Figure 1:
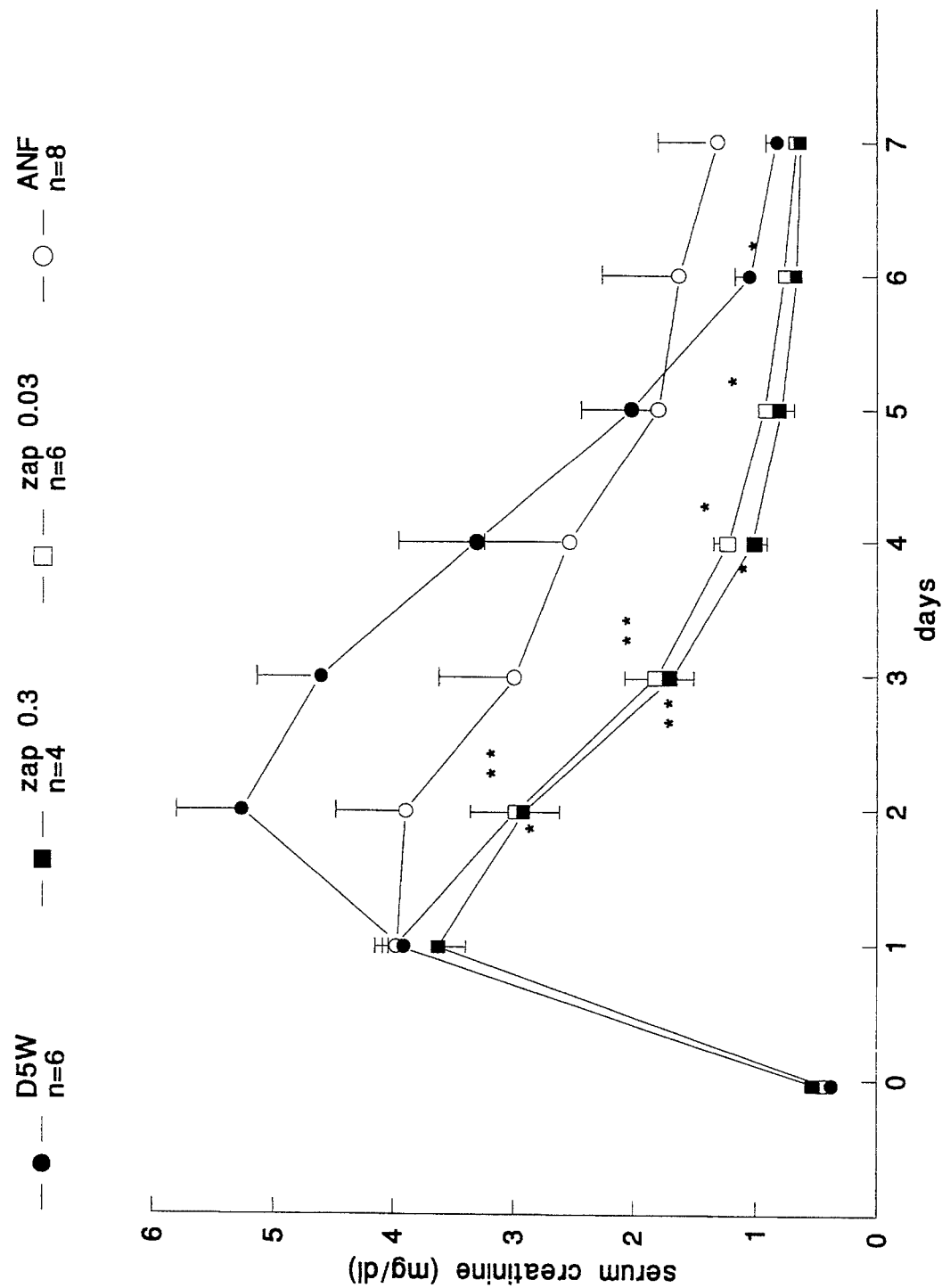
FIG. 1 is a graphical representation which shows the effect of zaprinast and ANF on established ischemic ARF. Serum creatinine (mg/dl) is plotted on the Y-axis against days on the X-axis. Serum creatinine was determined daily after 60 minutes of bilateral renal arterial clamping. Drugs were infused for four hours only on day 1. zap 0.3=zaprinast 0.3 mg/Kg/min, zap 0.03=zaprinast 0.03 mg/Kg/min, ANF= 200 ng/Kg/min. Values are the mean ± standard error of the mean of at least four determinations. **$p<0.01$, *$p<0.05$ versus $D_5W$ group.

In order to illustrate the invention in greater detail, the following specific laboratory examples were carried out. Although specific examples and details are illustrated herein, it will be appreciated that the invention is not limited to these specific examples or their details.

EXAMPLES

Methods

Renal injury and treatment. Male Sprague-Dawley rats (weight 320–400 grams) were fed standard rat chow (Purina) and allowed free access to tap water. On the day of surgery, rats were anesthetized with sodium pentobarbital given intraperitoneally (50 mg/kg). The kidneys were accessed through an abdominal midline incision and both the right and left renal arteries were occluded with smooth vascular clamps for 60 minutes. Twenty-four (24) hours after the ischemic insult, conscious restrained animals received four hour infusions, via the femoral vein, of either a 5% dextrose solution ($D_5W$), high dose zaprinast (0.30 mg/Kg/min), low dose zaprinast (0.03 mg/Kg/min), or ANF24 (0.2 µg/Kg/min). All drugs were dissolved in $D_5W$ and infused at a rate of 0.03 mls/minute.

Physiological parameters. The rat's femoral artery was catheterized with PE-50 tubing for blood pressure measurements. Mean arterial pressure (MAP) was measured every 30 minutes during the four hour drug infusion with a Harvard blood pressure monitor (model VT-15C). Urine was collected one hour prior to drug infusion and each hour during drug infusion for volume, sodium, and cGMP quantitation. At the end of the four hour drug infusion, rats were put into individual metabolic cages for three days, with free access to food and water, in order to quantitate daily urinary cGMP excretion. Urinary cGMP was measured using a commercial enzyme immunometric assay (EIA) (Caymen Chem. Ann Arbor, Mich.). Urine volume was measured gravimetrically, urine sodium was determined by flame photometry (Instrumentation Laboratory, model 943). Tail vein blood was collected daily for determination of serum creatinine. Two separate groups of rats underwent inulin clearance determinations twenty-four (24) hours after the infusion of zaprinast (0.03 mg/Kg/min) or vehicle. Inulin clearances were performed by conventional procedures published by Miller et al. (31).

Reagents. ANF24 (AP-III, U. S. Patent 4,496,544) and zaprinast were kindly provided by the Monsanto Company (St. Louis, Mo.). Inulin was purchased from Sigma Chemical Co. (St. Louis, Mo.).

Statistics. Statistics were performed using analysis software package (Instat, GraphPad, San Diego). All data were expressed as mean ± standard error of the mean (SEM).

Statistical analysis was performed by two-way analysis of variance and student's t-test was used to evaluate the significance of difference. A probability of less than 0.05 was considered statistically significant.

Figure 2:
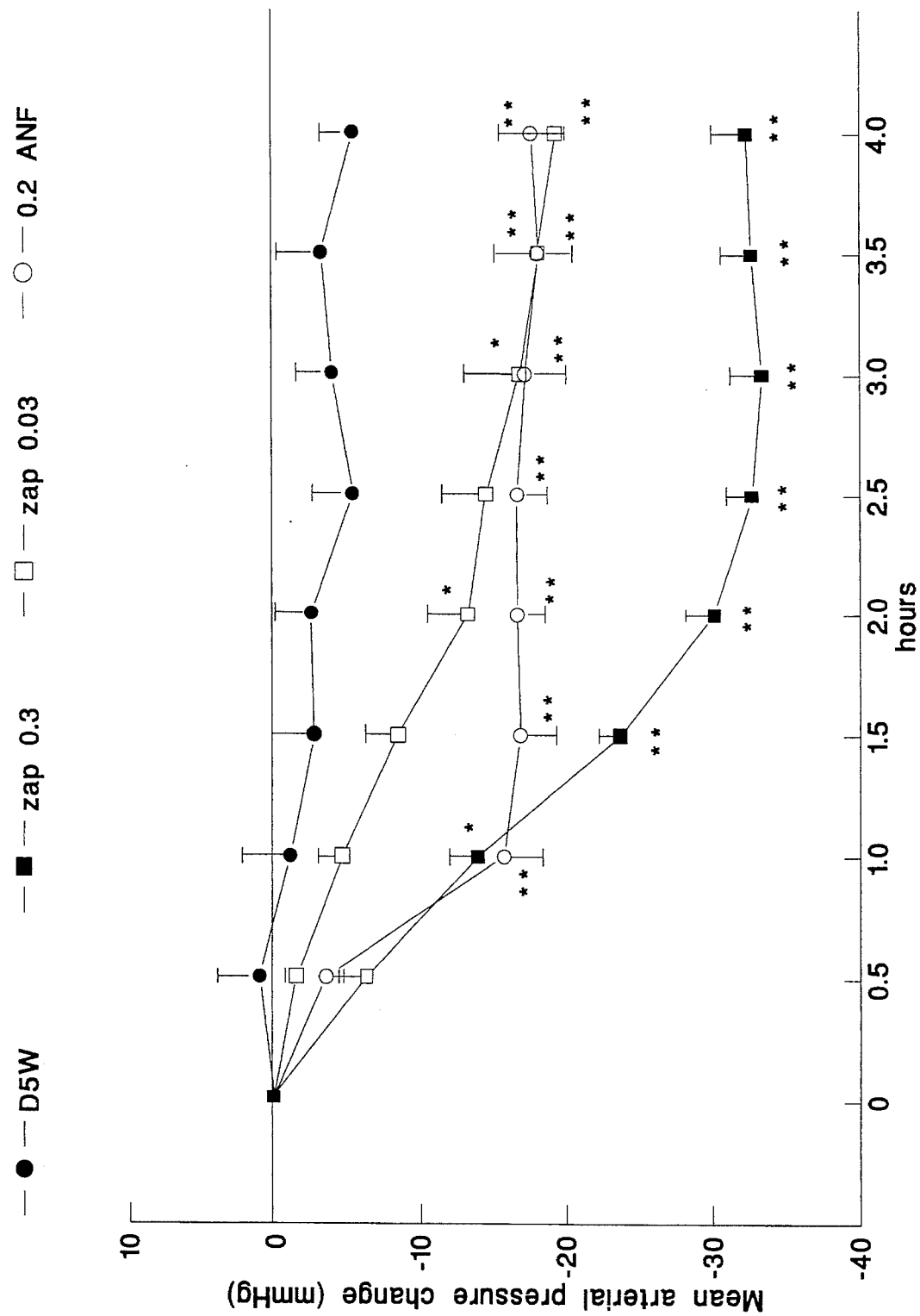
FIG. 2 is a graphical representation which shows the effect of zaprinast and ANF on mean arterial pressure (MAP) in established ischemic ARF. MAP Change (mmHg) is plotted on the Y-axis against hours on the X-axis. MAP was measured in awake rats every 30 minutes during drug infusion. The data is expressed as an absolute change in mmHg from MAP measured prior to drug infusion. zap 0.3=zaprinast 0.3 mg/Kg/min, zap 0.03=zaprinast 0.03 mg/Kg/min, ANF=200 ng/Kg/min. Values are expressed as the mean ± standard error of the mean of at least four determinations. **$p<0.01$, *$p<0.05$ versus $D_5W$ (a 5% dextrose solution).

Results. Sixty (60) minutes of bilateral renal artery clamping resulted in a significant decrease in renal function as measured by serum creatinine (FIG. 1). In order to ensure similar degrees of ischemia-induced ARF, only animals with 24-hour postischemic serum creatinine of 3.0 to 4.5 mg/dl were included for further study. Two days after renal ischemia, rats infused with $D_5W$ experienced a further decline in renal function as evidenced by a serum creatinine peak of 5.3±0.6 mg/dl. In contrast, animals receiving zaprinast experienced a significant increase in their renal function 24 hours after drug infusion. Serum creatinine decreased to 2.9±0.3 mg/dL and 3.0±0.4 mg/dL after treatment with low dose and high dose zaprinast respectively. Furthermore, serum creatinine levels remained significantly lower in the zaprinast-treated animals for six days post ischemia when compared to the vehicle-treated control group. Both low (0.03 mg/Kg/min) and high dose (0.30 mg/Kg/min) zaprinast proved to be equally efficacious. Since ANF has been demonstrated to ameliorate established ischemic ARF (9,10,15,16), it was elected to compare the relative potency of ANF (0.2 µg/Kg/min×4 hours) versus zaprinast on the test animals. This dose of ANF was chosen because it proved to be pharmacologically similar to low dose zaprinast in its ability to decrease mean arterial pressure (MAP) (FIG. 2). A trend was noted for ANF to decrease serum creatinine as compared to vehicle infusion; however, this did not reach statistical significance. Therefore, zaprinast is significantly more potent in alleviating established ischemic ARF when compared to ANF.

To ensure that serum creatinine measurements were a true reflection of renal function, GFR was determined by measuring inulin clearance. In two separate groups of animals, GFR was measured 24 hours after treatment with either $D_5W$ or zaprinast (0.03 mg/Kg/min). As seen in Table 1, below, GFR was significantly greater in the zaprinast-treated rats (0.94±0.29 mls/min/100 g B.W.) as compared to the vehicle-treated animals (0.14±0.04 mls/min/100 g B.W.). These data confirm that in these animals, serum creatinine is an accurate representation of renal function, and indeed zaprinast increases GFR in established ARF.

Figure 3:
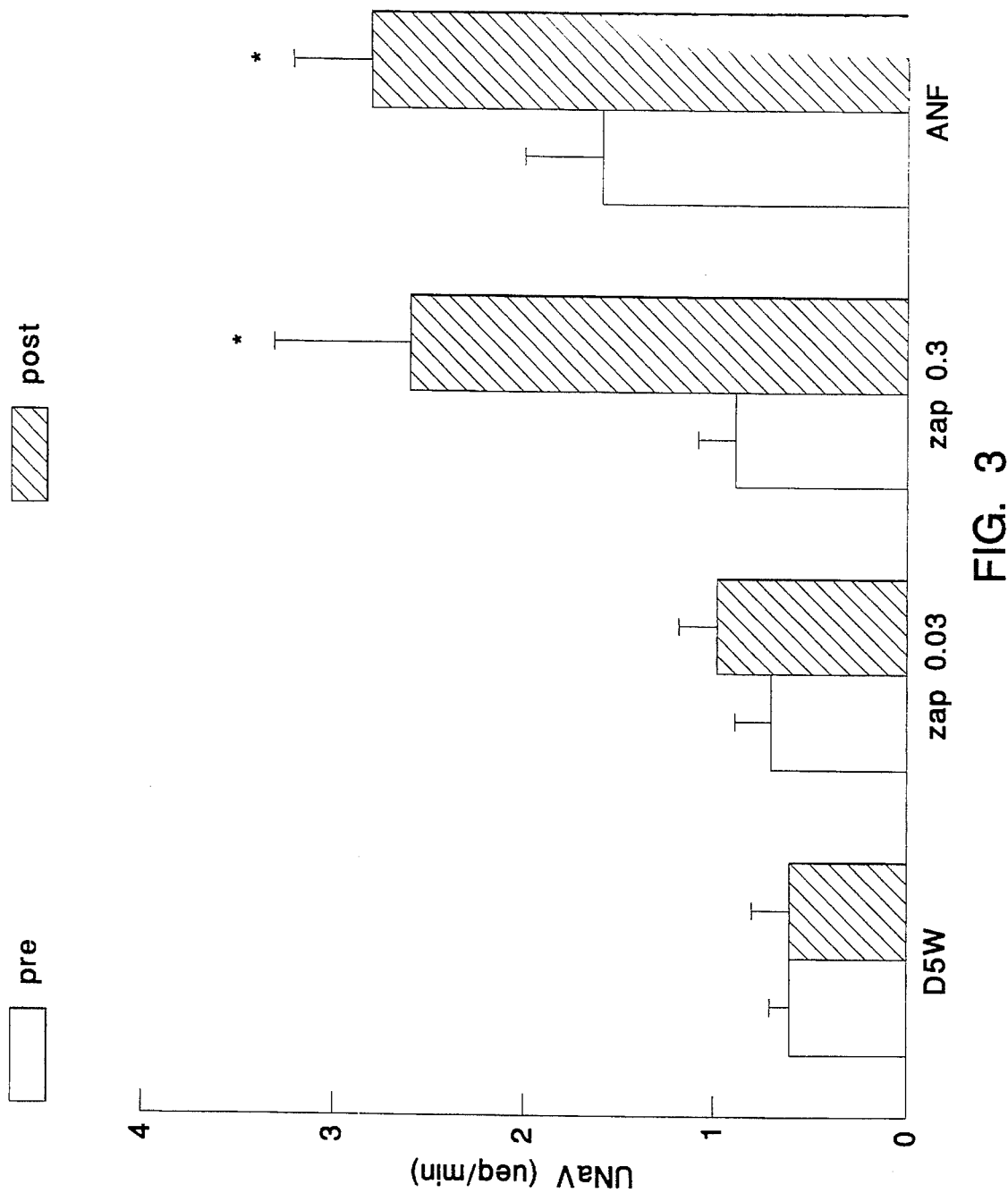
FIG. 3 is a bar graph which shows the effect of zaprinast and ANF on urinary sodium excretion ($U_{Na}V$) in established ARF. $U_{Na}V$ (µeq/min) levels are shown pre- and post-administration of drug. Rat urine was collected hourly during four hours of drug infusion. pre=$U_{Na}V$ before drug infusion, post=$U_{Na}V$ during the fourth hour of drug infusion. zap 0.3=zaprinast 0.3 mg/Kg/min, zap 0.03= zaprinast 0.03 mg/Kg/min, ANF=200 ng/Kg/min. Values are expressed as the mean ± standard error of the mean of at least four determinations. *$p<0.05$ versus pre $U_{Na}V$.
Figure 4:
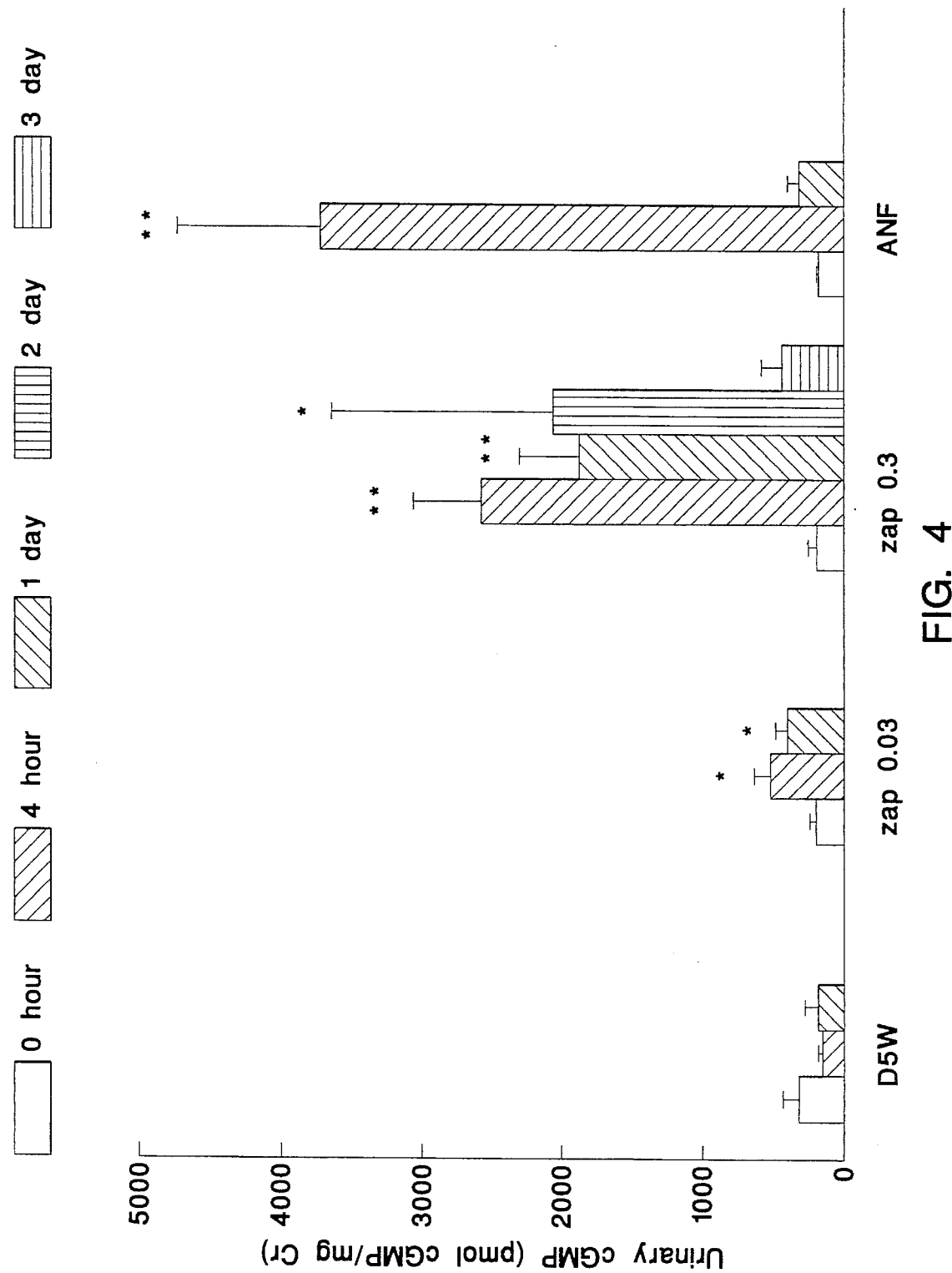
FIG. 4 is a bar graph which shows the effect of zaprinast and ANF on urinary cGMP excretion in established ARF. Urinary cGMP (pmol/cGMP/mg Cr) levels are shown pre-administration (0 hour) and at various times after administration of drug. Urine was collected hourly prior to and during drug infusion. After the drug infusions, animals were placed in individual metabolic cages and urine was collected for 24 hours. Urinary cGMP values were normalized for urinary creatinine levels in order to normalize for the degree of renal dysfunction in the various animal groups. Zap 0.3=zaprinast 0.3 mg/Kg/min, zap 0.03=zaprinast 0.03 mg/Kg/min, ANF=200 ng/Kg/min. Values are expressed as the mean ± standard error of the mean of at least four determinations. **$p<0.01$, *$p<0.05$ versus pre-drug infusion levels.

The beneficial effects of zaprinast on ARF demonstrated no dose-dependence. However, a clear dose-dependent relationship was established for blood pressure, urinary sodium excretion ($U_{Na}V$), and urinary cGMP excretion. High dose zaprinast maximally lowered MAP 34 mmHg, while MAP decreased only 20 mmHg in response to low dose zaprinast (FIG. 2). Sodium excretion was not altered by low dose zaprinast, while high dose zaprinast significantly increased $U_{Na}V$, two-fold, during the fourth hour of drug infusion. (FIG. 3). ANF increased urinary sodium excretion comparable to that of high dose zaprinast (FIG. 3). Lastly, urinary cGMP excretion (fmoles/mg creatinine) increased from basal levels of 210±29 to 519±103 in response to low dose zaprinast and 2570±486 after four hours of high dose zaprinast infusion (FIG. 4). ANF increased urinary cGMP excretion to a similar degree as high dose zaprinast.

ANF has been demonstrated to have a short circulating halflife even in nephrectomized animals (32); therefore, renal cGMP synthesis should return to basal levels soon after the end of the ANF infusion. Because the metabolism and clearance of zaprinast is currently unknown, evaluation was made of the synthesis of cGMP in the kidney for three days following the end of the zaprinast infusion. As seen in FIG. 4, urinary cGMP excretion remained significantly elevated 48 hours after the end of the high dose zaprinast infusion, and did not return to pre-drug level until three days after drug infusion. In contrast, urinary cGMP excretion returned to basal levels 24 hours after the end of the ANF infusion. Therefore, it was hypothesized that the increased potency of zaprinast compared to ANF may be secondary to its prolonged biological effects on the kidney.

TABLE 1

| group | serum creatinine (mg/dl) | inulin clearance (mls/min/100 g B.W.) |
|---|---|---|
| $D_5W$ | 4.35 ± 0.79 | 0.14 ± 0.04 |
| zap 0.03 | 1.85 ± 0.20* | 0.94 ± 0.29* |

TABLE 1 shows the effect of zaprinast on glomerular filtration rate (GFR) in established ARF. Forty-eight (48) hours after drug infusion, blood was collected for serum creatinine and GFR was determined by inulin clearances. Zap 0.03=zaprinast 0.03 mg/Kg/min. Values are expressed as the mean ± standard error of the mean of four determinations. *p<0.05 versus $D_5W$ group.

The administration of the zaprinast to a host or patient manifesting acute renal failure can be carried out by conventional means, preferably in formulations with pharmaceutically acceptable diluents and carriers. The amount to be administered must be an effective amount, that is, an amount which is medically beneficial but does not present toxic effects which overweigh the advantages which accompany its use.

It is expected that the adult human dose would range upward from about 100 mg of the active drug and preferably in a daily dose of from about 1.5 to about 15 mg/Kg of body weight. A suitable route of administration is orally in the form of capsules, tablets, syrups, elixirs and the like, although parenteral administration can also be used such as , e.g., intravenous administration in admixture with physiologic saline and/or suitable buffers. Appropriate formulations of the active drug in pharmaceutically acceptable diluents and carriers in therapeutic dosage form can be prepared by reference to general texts in the field well known to the person skilled in the art such as, e.g., *Remington's Pharmaceutical Sciences*, Ed. Arthur Osol, 16th ed. 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

REFERENCES

1. Burnier M. and Schrier P. W.: Protection from acute renal failure. Adv Exp Med Biol 212: 275–283, 1987
2. Finn W. F.: Recovery from acute renal failure. In: Brenner B. M. and Lazarus J. M. (eds): Acute renal failure. Churchill Livingstone, New York. pp. 875–918, 1988
3. Leichtman A. B., Goldszer R. C., Strom T. B. and Tilney N. L.: Acute renal failure associated with renal transplantation. In: Brenner B. M. and Lazarus J. M. (eds): Acute renal failure. Churchill Livingatone, New York. pp. 659–673, 1988
4. Tanner G. A., Sloan K. L. and Sophasan S.: Effect of renal artery occlusion on kidney function in the rat. Kidney Int 4: 377–389, 1973
5. Pollock D. M. and Arendshorst W. J.: Effect of atrial natriuretic factor on renal hemodynamics in the rat. Am J Physiol 251 (Renal Fluid Electrolyte Physiol. 20): F795–F801, 1986

6. Maack T., Atlas S. A., Camargo M. J. F. and Cogan M. G.: Renal hemodynamic and natriuretic effects of atrial natriuretic factor. Federation Proc, 45: 2128–2132, 1986
7. Dunn B. R., Ichikawa I., Pfeifer J. M., Troy J. L. and Brenner B. M.: Renal and systemic hemodynamic effects of synthetic atrial natriuretic pepfide in the anesthetized rat. Circ Res 59: 237–246, 1986
8. Needleman P., Adams S. P., Cole B. R., Currie M. G., Geller D. M., Michener M. L., Saper C. B., Schwartz D. and Standaen D. G.: Atriopeptins as cardiac hormones. Hypertension 7: 469– 482, 1985
9. Gianello P., Poelaert D., Ramboux A., Squiffiet J. P., Berbinschi A., Donckier J., Ketelslegers J. M., Lambotte L. and Alexander G.: Beneficial effect of atrial natriuretic factor on ischemically injured kidneys in the rat. A new approach to improve early renal function. Transplantation 45: 860–863, 1988
10. Nakamoto M., Shapiro J. I., Shanley P. F., Chan L. and Schrier R. W.: In vitro and in vivo protective effect of atriopeptin III on ischemic acute renal failure. J Clin Invest 80:698–705, 1987
11. Shaw S., Weidmann P. and Zimmermann A.: Urodilatin, not nitroprosside, combined with dopamine reverses ischemic acute renal failure. Kidney Int 42: 1153–1159, 1992
12. Pollock D. M. and Opgenorth T. J.: Beneficial effect of the ANF analog A68828 on recovery from ischemic acute renal failure. Renal Failure 14(2): 141–146, 1992
13. Akabane S., Imanishi M., Matsushima Y., Kawamura M., Kuramochi M., Ito K. and Omae T.: Renal actions of atrial natriuretic pepfide on the postischemic kidney. Can J Physiol Pharmacol 66:601–607, 1988
14. Pollock D. M., Hoist M. and Opgenorth T. J.: Effect of the ANF analog A68828 in cisplatin-induced acute renal failure. J Pharmacol Exp Ther 257:1179–1183, 1991
15. Conger J. D., Falk S. A. and Hammond W. S.: Atrial natriuretic pepfide and dopamine in established acute renal failure in the rat. Kidney Int 40: 21–28, 1991
16. Rahman S. N., Kim G. E., Mathew A. S., Goldberg C. A., Aligren R., Schrier R. W. and Conger J. D.: Effects of atrial natriuretic peptide in clinical acute renal failure. Kidney Int. 45: 1731–1738, 1994
17. Gianello P., Ramboux A., Poelan D., Jamart J., Berbinschi A., Donckier J., Ketelslegers J. M., Lambotte L., Squiffiet P. and Alexander G. P. J.: Prevention of acute cyclosporine nephrotoxicity by atrial natriuretic factor after ischemia in the rat. Transplantation 47: 512–515, 1989
18. Capasso G., Rosati C., Ciani F., Giordano D. R., Russo F. and De Santo N. G.: The beneficial effect of atrial natriuretic peptide on cyclosporine nephrotoxicity. Am J Hypertens 3: 204–210, 1990
19. Waldman S. A., Rapoport R. M. and Murad F.: Atrial natriuretic factor selectively activates particulate guanylate cyclase and elevates cyclic GMP in rat tissues. J Biol Chem 259: 14332–14334, 1985
20. Light D. B., Schwieben E. M., Karlson K. H. and Stanton B. A.: Atrial natriuretic peptide inhibits a cation channel in renal inner medullary collecting duct cells. Science 243: 383–385, 1989
21. Leitman D. C., Agnost V. L., Tuan J. J., Andresen Y. W. and Murad F.: Atrial natriuretic factor and sodium nitroprusside increase cyclic GMP in cultured rat lung fibroblasts by activating different forms of guanylate cyclase. J Blochem 244: 69–74, 1987
22. Chintala M. S., Chiu P. J. S., Vemulapalli S., Watkins R. W. and Sybertz E. J.: Inhibition of endothelial derived relaxing factor (EDRF) aggravates ischemic acute renal failure in anesthetized rats. Naunyn-Schmiedeberg's Arch Pharmacol 348: 305–310, 1993
23. Noguchi S., Kashihara Y., Ikegami Y., Morimoto K., Miyamoto M. and Nakao K.: Insulin-like growth factor-1 ameliorates transient ischemia-induced acute renal failure in rats. J Pharmacol Exp Ther 267: 919–926, 1993
24. Thompsom W. J.: Cyclic nucleotide phosphodiesterases: pharmacology, biochemistry and function. Pharmac ther 51: 13–33, 1991
25. Weishaar R. E.: Multiple molecular forms of phosphodiesterase: an overview. J Cyclic Nucleotide and protein Phosphorylation Research 11: 463–472, 1987
26. Beavo J. A.: Multiple isozymes of cyclic nucleotide phosphodiesterase. Advances in Second Mesenger and Phosphoprotein Research 22: 1–38, 1988
27. Pang D. C.: Cyclic AMP and cyclic GMP phosphodiesterases: target for drug development Drug Development Research 12: 85–92, 1988
28. Dundore R. L., Clas D. M., Wheeler L. T., Habeeb P. G., Bode D. C., Buchholz R. A., Sliver P. J. and Pagani E. D.: Zaprinast increases cyclic GMP levels in plasma and aortic tissue of rats. Eur J Pharmacol 249: 293–297, 1993
29. McMahon E. G., Palomo M. A., Mehta P. and Olins G. M.: Depressor and natriuretic effects of M&B 22,948, a guanosine cyclic 3',5-monophosphate-selective phosphodiesterase inhibitor. J Pharmacol Exp Ther 251: 1000–1005, 1989
30. Buchholz R. A., Dundore R. L., Pratt P. F., Hallenbeck W. D., Wassey M. L. and Silver P. J.: The selective phosphodiesterase I inhibitor zaprinast (ZAP) potentiates the hypotensive effect of sodium nitroprusside (SNP) in conscious SHR. Fed Am Soc Exp Biol J 3: A1186, 1989
31. Miller S. B., Maxtin D. R., Kissane J. and Hammerman M. R.: Insulin-like growth factor I accelerates recovery from ischemic acute tubular necrosis in the rat. Proc Nail Aced Sc USA 89:11876–11880, 1992
32. Katsube N., Schwartz D. and Needleman P.: Atriopeptin turnover: quantitative relationship between in vivo changes in plasma levels and atrial content. J Pharmacol Exp Ther 239: 474–479, 1986
33. Kjellstrand C. M., Berkseth R. O. and Klinkmann H.: Treatment of acute renal failure. In: Schrier R. W. and Gottschalk C. W. (eds): Diseases of the kidney. Little, Brown and Company, Boston/Toronto, pp. 1501–1540, 1988
34. Levinsky N. G. and Bernard D. B.: Mannitol and loop diuretics in acute renal failure. In: Brenner B. M. and Lazarus J. M. (eds): Acute renal failure. Churchill Livingatone, New York. pp. 841–856, 1988
35. Garbers D.: The guanylyl cyclase receptor family. The New Biologist 2(6): 499–504, 1990
36. Bennett B. D., Bennett G. L., Vitangcol R. V., Jeweli J. R. S., Bumier J., Henzel W. and Lowe D. G.: Extracellular Domain-IgG fusion proteins for three human natriuretic peptide receptors. Hormone pharmacology and application to solid phase screening of synthetic peptide antisera. J Biol Chem 266: 23060–23067, 1991
37. Maack T., Suzuki M., Alineida F. A., Nussenzveig D., Scarborough R. M., McEnroe G. A. and Lewicki J. A.: Physiological role of silent receptors of atrial natriuretic factor. Science 238: 675–678, 1987
38. Nussenzveig D. R., Lewicki J. A. and Maack T.: Cellular mechanisms of the clearance function of type C receptors of atrial natriuretic factor. J Biol Chem 265: 20952–20958, 1990.
39. Wilkins M. R., Settle S. L., Stockmann P. T. and Needleman P.: Maximizing the natriuretic effect of endogenous atriopoptin in a rat model of heart failure. Proc And Aced Sci USA 87: 6465–6469, 1990

40. Keohn J. A., Norman J. A., Jones B. N., LeSueur L., Sakane Y. and Ghai R. D.: Degradation of atrial natriuretic factor by kidney cortex membranes. J Biol Chem 262: 11623–11627, 1987

41. Olins G. M., Spear K. L., Siegel N. R., Reinhard E. J. and Zurcher-Neely H. A.: Atrial peptide inactivation by rabbit-kidney brush-border membranes. Eur J Biolchem 170: 431–434, 1987

42. Sudoh T., Minamino N., Kangawa K., Matsuo H.: C-type natriuretic peptide (CNP): a new member of natriuretic peptide family identified in porcine brain. Bioch Biophys Res Commun 168:863–870, 1990.

43. Greenwald J. E., Needleman P., Wilkins M. and Schreiner G. F.: Renal synthesis if an atripeptin-like protein in physiology and pathophysiology. Am J Physiol 260 (Renal Fluid Electrolyte Physol 29): F602–F607, 1991

44. Ritter D., Needleman P. and Greenwald J. E.: Synthesis and secretion of an atriopeptin-like protein in rat kidney cell culture. J Clin Invest 87: 208–212, 1991

45. Ritter D., Chao J. L., Needleman P., Tetens E. and Greenwald J. E.: Localization, synthetic regulation, and biology of renal atripeptin-like prohormone. Am J Physiol 263 (Renal Fluid Electrolyte Physol 32): F503–F509, 1992

46. Dean A. D., Vehaskari V. M. and Greenwald J. E.: Synthesis and localization of C-type natriuretic peptide in mammalian kidney. Am J Physiol 266 (Renal Fluid Electrolyte Physol 35): F491–F496, 1994

What is claimed is:

1. A method for the treatment of acute renal failure comprising administering to a warm-blooded mammal manifesting acute renal failure a small but effective amount of zaprinast sufficient to effect acceleration of the recovery from said acute renal failure.

2. The method of claim 1 in which the amount of zaprinast administered is from about 1.5 to about 15 mg/Kg per day.

3. The method of claim 1 in which the acceleration of the recovery is determined by comparing the serum creatinine level of the treated mammal with a standard control level.

4. The method of claim 1 in which the acute renal failure is caused by ischemic injury.

* * * * *